(12) United States Patent
Ikebukuro et al.

(10) Patent No.: US 9,683,238 B2
(45) Date of Patent: Jun. 20, 2017

(54) VASCULAR ENDOTHELIAL GROWTH FACTOR-BINDING APTAMERS

(71) Applicants: NATIONAL UNIVERSITY CORPORATION TOKYO UNIVERSITY OF AGRICULTURE AND TECHNOLOGY, Tokyo (JP); JNC CORPORATION, Tokyo (JP)

(72) Inventors: Kazunori Ikebukuro, Tokyo (JP); Yoshihiko Nonaka, Tokyo (JP)

(73) Assignees: National University Corporation Tokyo University of Agriculture and Technology, Tokyo (JP); JNC Corporation, Tokyo (JP)

( * ) Notice: Subject to any disclaimer, the term of this patent is extended or adjusted under 35 U.S.C. 154(b) by 0 days.

(21) Appl. No.: 14/655,622

(22) PCT Filed: Dec. 12, 2013

(86) PCT No.: PCT/JP2013/083344
§ 371 (c)(1),
(2) Date: Jun. 25, 2015

(87) PCT Pub. No.: WO2014/103738
PCT Pub. Date: Jul. 3, 2014

(65) Prior Publication Data
US 2015/0376620 A1 Dec. 31, 2015

(30) Foreign Application Priority Data
Dec. 28, 2012 (JP) .................... 2012-288934

(51) Int. Cl.
| | |
|---|---|
| C12N 15/11 | (2006.01) |
| C12N 15/115 | (2010.01) |
| G01N 33/53 | (2006.01) |
| G01N 33/74 | (2006.01) |

(52) U.S. Cl.
CPC ....... *C12N 15/115* (2013.01); *G01N 33/5308* (2013.01); *G01N 33/74* (2013.01); *C12N 2310/16* (2013.01); *G01N 2333/475* (2013.01); *G01N 2333/515* (2013.01)

(58) Field of Classification Search
None
See application file for complete search history.

(56) References Cited

FOREIGN PATENT DOCUMENTS

| EP | 1700912 A1 | 9/2006 |
|---|---|---|
| JP | 2008-237042 A | 10/2008 |
| JP | 2011-92138 A | 5/2011 |
| WO | WO 2005/049826 A1 | 6/2005 |

OTHER PUBLICATIONS

Fukaya et al., "Improvement of VEGF-binding ability of DNA aptamer by in silico maturation and its characterization," 92nd Annual Meeting of the Chemical Society of Japan, vol. 92, No. 3, 2012, 1 page (abstract).
Ikebukuro et al., "A novel method of screening thrombin-inhibiting DNA aptamers using an evolution-mimicking algorithm," Nucleic Acids Research, vol. 33, No. 12, 2005 (published online Jul. 7, 2005), pp. 1-7.
Ikebukuro et al., "Improvement of DNA aptamers which bound to VEGF by in silico maturation," 91st Annual Meeting of the Chemical Society of Japan, vol. 92, No. 3, Mar. 2011, 1 page (abstract).
Ikebukuro et al., "Improvement of Function of Aptamer Using Evolution Mimicking Algorithm," The Chemical Society of Japan, vol. 26, 2008, pp. 78-82 with a partial translation.
International Search Report dated Mar. 18, 2014, for International Application PCT/JP2013/083344.
Nonaka et al., "Affinity improvement of a VEGF aptamer by insilico maturation for sensitive VEGF-detection system," Analytical Chemistry, vol. 85, 2013 (published online Dec. 13, 2012), 26 pages.
Nonaka et al., "Development of VEGF-binding aptamer for rapid VEGF-detection with in silico maturation method," Abstract of Autum Meeting of the Electrochemical Society of Japan, 2011, 4 pages.
Nonaka et al., "Screening and Improvement of an Anti-VEGF DNA Aptamer," Molecules, vol. 15, Jan. 7, 2010, pp. 215-225.
Savory et al., "Selection of DNA aptamer against prostate specific antigen using a genetic algorithm and application to sensing," Biosens Bioelectron., vol. 26, No. 4, Dec. 15, 2010 (published online Jul. 21, 2010), 1 page (abstract).
Tuerk et al., "Systematic Evolution of Ligands by Exponential Enrichment: RNA Ligands to Bacteriophage T4 DNA Polymerase," Science, New Series, vol. 249, No. 4968, Aug. 3, 1990, pp. 505-510.

*Primary Examiner* — Kate Poliakova-Georgantas
(74) *Attorney, Agent, or Firm* — Birch, Stewart, Kolasch & Birch, LLP

(57) ABSTRACT

Disclosed is providing a novel VEGF-binding aptamer whose affinity to VEGF is higher than those of known VEGF-binding aptamers. By an in silico maturation method starting from a known VEGF-binding aptamer, 4 kinds of aptamers whose affinities to VEGF are higher than that of the known VEGF-binding aptamer were prepared. By linking two molecules of an obtained aptamer to each other via a linker, an aptamer having an even higher affinity to VEGF was obtained. The polynucleotide of the present invention contains the base sequence of any one of SEQ ID NOs:1 to 4, and binds to vascular endothelial growth factor.

11 Claims, 2 Drawing Sheets

VASCULAR ENDOTHELIAL GROWTH FACTOR-BINDING APTAMERS

TECHNICAL FIELD

The present invention relates to a novel aptamer that binds to vascular endothelial growth factor (which may be hereinafter referred to as "VEGF").

BACKGROUND ART

VEGF binds to a receptor present in vascular endothelial cells to promote growth of the endothelial cells, thereby promoting angiogenesis. VEGF is therefore attracting attention from the viewpoint of its association with diseases in which angiogenesis plays an important role. For example, VEGF is reported to show an elevated serum level in patients with solid tumors. Thus, substances that bind to VEGF are expected to be sensor elements useful for diagnosis of various diseases accompanied by angiogenesis.

Measurement of a test substance such as a protein in a sample is carried out mainly by an immunoassay at present. Various immunoassay methods are known and practically used, and any of these methods uses an antibody specific to the test substance. Although antibodies specific to test substances can be prepared by conventional methods, the methods are laborious, and specific antibodies are therefore expensive.

On the other hand, aptamers, which are polynucleotide molecules that specifically bind to arbitrary molecules, are known. Since total chemical synthesis of aptamers can be carried out using a commercially available nucleic acid synthesizer, aptamers are much less expensive than specific antibodies, and can be easily modified. Therefore, their practical use as sensor elements has been expected. An aptamer that specifically binds to a desired target molecule can be prepared by a method called SELEX (Systematic Evolution of Ligands by EXponential Enrichment) (Non-patent Document 1). In this method, the target molecule is immobilized on a carrier, and a nucleic acid library composed of nucleic acid having vast kinds of random base sequences is added thereto, followed by recovering nucleic acid binding to the target molecule. The recovered nucleic acid is amplified by PCR, and then added again to the carrier on which the target molecule is immobilized. By repeating this process about 10 times, aptamers having high binding capacities to the target molecule are concentrated, and their sequences are determined to obtain aptamers that recognize the target molecule. The nucleic acid library can be easily prepared by randomly binding nucleotides using an automated chemical synthesizer for nucleic acid. Thus, by a method which positively utilizes contingency by using a nucleic acid library containing random base sequences, an aptamer which specifically binds to an arbitrary target substance can be prepared.

The present inventors previously succeeded in obtaining an aptamer that binds to VEGF by SELEX which utilizes a method comprising: binding a desired target substance to nucleic acid in a nucleic library in the presence of a carrier on which a non-target substance is immobilized; recovering only nucleic acid bound to the desired target substance; amplifying the recovered nucleic acid by PCR; obtaining single-stranded nucleic acid from the amplified product to provide a nucleic acid library; bringing the nucleic acid library into contact with an area on which the target substance is immobilized; recovering nucleic acid bound to the solid phase; similarly amplifying the recovered nucleic acid by PCR; obtaining single-stranded nucleic acid therefrom to provide a nucleic acid library; bringing the nucleic acid library again into contact with areas on each of which the target substance or the non-target substance is immobilized; and then repeating this cycle in the same manner (Patent Document 1).

PRIOR ART DOCUMENTS

Patent Documents

[Patent Document 1] JP 2008-237042 A
[Patent Document 2] WO 2005/049826

Non-Patent Documents

[Non-patent Document 1] Tuerk, C. and Gold L. (1990), Science, 249, 505-510
[Non-patent Document 2] Kazunori Ikebukuro et Nucleic Acids Research, 33(12), e108
[Non-patent Document 3] Nasa Savory et al., Biosensors and Bioelectronics, Volume 26, Issue 4, 15 Dec. 2010, Pages 1386-1391

SUMMARY OF THE INVENTION

Problems to be Solved by the Invention

In order to highly sensitively measure VEGF, an aptamer having a high affinity to VEGF is required. Accordingly, an object of the present invention is to provide a novel VEGF-binding aptamer whose affinity to VEGF is higher than (that is, whose dissociation constant is lower than) those of the known VEGF-binding aptamers described in Patent Document 1.

Means for Solving the Problems

SELEX basically enables preparation of an aptamer for almost any target substance. However, in some cases, screening of an aptamer having high binding capacity by SELEX is unsuccessful because of the following reasons. In the experimental operation of SELEX, the diversity of the random sequence pool is limited[29]. In many cases, the concentration of the sequence pool is less than 1 μM (which equals $1.0 \times 10^{-6}$ M), and the experimental operation is carried out in a 1.5-mL sample tube (which equals $1.5 \times 10^{-3}$ L). As a result, $1.5 \times 10^{-9}$ mol (which equals $1.0 \times 10^{15}$ molecules) of nucleotides can be contained in the manipulated sample. On the other hand, the diversity of a 30-mer random library is $4^{30}$ (which is almost equivalent to $10^{18}$). Thus, only 1/1000 of the total candidates can be evaluated in a common operation of SELEX. Moreover, the secondary structure of each oligonucleotide influences the amplification efficiency in PCR (the references 30 and 31 listed below). Aptamers normally have particular secondary structures which are necessary for specifically recognizing their target molecules, and amplification of oligonucleotides having higher order structures by PCR in SELEX might be difficult. Thus, the efficiency of obtaining such target-binding sequences by SELEX is low.

In view of this, the present inventors subjected a part of the bases in the base sequence of VEap121 (SEQ ID NO:5), which is a VEGF-binding aptamer described in Patent Document 1, to the in silico maturation method to alter the base sequence, and succeeded in further increasing the affinity of the aptamer to the gene product. The in silica maturation method is a method invented by a co-inventor of the present application, and described in Non-patent Document 2, Non-patent Document 3, and Patent Document 2. That is, mutation is allowed to occur in silico, and aptamers having various mutated base sequences are chemically synthesized, followed by measuring the binding capacities of these aptamers to VEGF. Aptamers having high binding affinities are selected, and the selected aptamers are further mutated in silico, followed by chemically synthesizing the mutated aptamers and measuring the binding capacities of the synthesized aptamers to VEGF. This process is carried out repeatedly. Since VEap121, which is described in Patent Document 1, is considered to have a G-quadruplex structure, bases other than guanine bases which are considered to be necessary for maintenance of the G-quadruplex structure were partially mutated by the method concretely described in the Examples below.

By the in silico maturation method starting from VEap121, the present inventors succeeded in preparation of 4 kinds of aptamers whose affinities to VEGF are higher than that is, whose dissociation constants for VEGF are lower than, that of VEap121. The present inventors also succeeded in obtaining an aptamer having an even higher affinity to VEGF by linking two molecules of an obtained aptamer to each other via a linker, thereby completing the present invention.

That is, the present invention provides a polynucleotide comprising the base sequence of any one of SEQ ID NOs:1 to 4, which polynucleotide binds to vascular endothelial growth factor. The present invention also provides a method for measuring vascular endothelial growth factor in a test sample, which method comprises bringing the polynucleotide of the present invention into contact with vascular endothelial growth factor, and measuring binding therebetween. The present invention also provides a kit for measuring vascular endothelial growth factor, comprising the polynucleotide of the present invention.

Effect of the Invention

By the present invention, a novel VEGF-binding aptamer whose affinity to VEGF is higher than those of known VEGF-binding aptamers was provided.

BRIEF DESCRIPTION OF THE DRAWINGS

FIG. 3a shows the difference between the parent sequence (VEap121) and a sequence improved by in silica maturation (3R02). FIG. 3b shows the difference between 3R02 and 3R02 bivalent. From the raw CD spectrum of 3R02 bivalent, the raw CD spectrum of T10 was subtracted. The spectrum obtained by the subtraction is shown in this figure. The X-axis represents the frequency, and the Y-axis represents the mean residue molar ellipticity.

MODE FOR CARRYING OUT THE INVENTION

Figure 1:
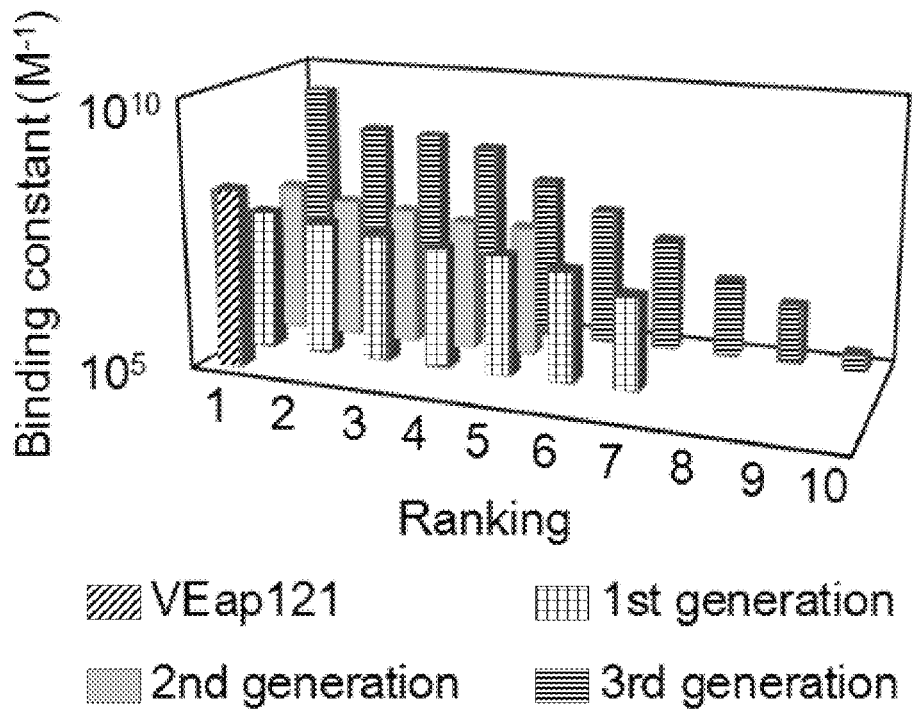
FIG. 1 is a diagram showing VEGF-binding capacities of oligonucleotides obtained from three generations of in silica maturation carried out in the Examples below. The X-axis represents the ranks of the oligonucleotides in each generation evaluated based on $K_d$. The Y-axis represents the binding constant of each oligonucleotide. In this diagram, oligonucleotides having no binding capacity to VEGF are not shown.

VEGF is secreted as a plurality of isoforms formed by alternative splicing of exons. The most basic isoform is $VEGF_{165}$, which has strong physiological activity. The second basic isoform of VEGF, which is biologically weaker, is $VEGF_{121}$. Although the receptor-binding domain is identical between $VEGF_{165}$ and $VEGF_{121}$, only $VEGF_{165}$ has a heparin-binding domain.

As concretely described in the Examples below, by the in silico maturation method starting from VEap121 (which binds to both $VEGF_{165}$ and $VEGF_{121}$), which is described in Patent Document 1, the present inventors succeeded in preparation of four kinds aptamers whose affinities to VEGF are higher than, that is, whose dissociation constants are low than, that of VEap121. The base sequences of these four kinds of aptamers are shown in SEQ ID NO:1 to SEQ ID NO:4. Among these, the aptamer named 3R02, which has the base sequence of SEQ ID NO:1, has an especially high affinity to VEGF, which is preferred.

In the Examples below, it was shown that the aptamer in which two molecules of 3R02, each having the base sequence of SEQ NO:1, are linked to each other via a linker composed of 10 thymines has an especially high affinity to VEGF. From this, it can be seen that a region having the base sequence of any one of SEQ ID NOs:1 to 4 is likely to maintain its binding capacity to VEGF even in cases where another base sequence is linked to its end as long as the whole aptamer structure having the base sequence of any one of SEQ NOs:1 to 4 is contained in the region. In particular, an aptamer in which a base sequence composed of one or several bases is linked to one end or both ds of the base sequence of any one of SEQ ID NOs:1 to 4 is considered to be likely to maintain its affinity to VEGF. Accordingly, the present invention provides a polynucleotide which contains the base sequence of any one of SEQ ID NOs:1 to 4 and binds to VEGF.

As can be seen from the Examples below, a polynucleotide wherein a plurality of, preferably two, polynucleotide molecules each having the base sequence of any one of SEQ ID NOs:1 to 4 are linked to each other directly or via a linker(s) is also preferred. Such a polynucleotide is likely to have a higher affinity to VEGF than the individual unlinked polynucleotides. The polynucleotide which was actually prepared in the Examples below, in which two polynucleotides each having the base sequence of SEQ ID NO:1 are linked to each other via a linker, is especially preferred. In cases where a plurality of polynucleotide molecules are linked to each other via a linker(s), the linker is not limited as long as the base sequence of the linker does not adversely affect the affinity to VEGF, and a polynucleotide composed of identical bases such as polythymine (t) is preferred since the polynucleotide itself does not cause intramolecular hybridization or the like. The size of the linker is not limited, and usually about 5 bases to 20 bases. In cases where not less than three polynucleotide molecules are linked to each other, the polynucleotide molecules do not necessarily need to be linearly linked. For example, the polynucleotide molecules may be linked to each other to form a radial shape or a dendrimer.

The dissociation constant of the polynucleotide of the present invention for VEGF is preferably less than 3 nM, more preferably less than 1 nM. The dissociation constant can be measured by a well-known method, and the method is also described in the Examples below.

The VEGF-binding aptamer of the present invention was created by the novel method which is described in the Examples below in detail. Since the base sequence of the aptamer was revealed by the present invention, the aptamer can be easily chemically synthesized using a commercially available nucleic acid synthesizer.

Since the novel aptamer having a high affinity to VEGF was provided by the present invention, VEGF in a test sample can be highly sensitively measured using the aptamer. The aptamer can be used for detection and quantification of the target substance, VEGF, by a per se well-known method. As the test sample, a body fluid such as serum or plasma, or a diluent thereof may be used. The detection or quantification of VEGF in a test sample using the aptamer of the present invention can be carried out by a well-known normal method using an aptamer, and examples of the method include sandwich immunoassays, competition immunoassays, and immunochromatography methods, including Enzyme Linked Immunosorbent Assays (ELISA), in which the aptamer of the present invention is used instead of an antibody. Since an anti-VEGF antibody is commercially available, a sandwich method in which VEGF is sandwiched between the anti-VEGF antibody and the aptamer of the present invention is also possible. The measurement can also be carried out using the measurement method based on an aptameric enzyme subunit (WO 2005/049826) or on a capturable aptamer (WO 2007/086403 or WO 2008/038696), which was developed by the present inventors and can be carried out only with an aptamer. The detection and quantification of VEGF can also be carried out by a well-known method such as the aptamer blotting method or the surface plasmon resonance (SPR) method as concretely described in the Examples below.

The present invention also provides a VEGF measurement kit containing an aptamer of the present invention, which kit is used for such measurement of VEGF. Such a kit may contain, for example, an aptamer of the present invention labeled with a fluorescent label, enzyme label, chemiluminescent label, or radiolabel; a solid phase on which an aptamer of the present invention is immobilized; a necessary buffer; and/or the like. The kit may be the same as a well-known kit except that the kit contains an aptamer of the present invention.

The present invention is concretely described below by way of Examples. However, the present invention is not limited to the Examples below.

EXAMPLES

Materials

All synthetic oligonucleotides were purchased from Greiner Bio-One (Japan). A recombinant human $VEGF_{165}$ (which is expressed in Sf21 insect cells) and a biotinylated anti-VEGF antibody (BAF293) were purchased from R&D Systems (United States). Fetal Bovine serum (BSA) was purchased from SIGMA-Aldrich (Japan). A nitrocellulose membrane (Amersham (registered trademark) Hybond (registered trademark)-ECL) was purchased from GE Healthcare (United States). Immobilon Western chemiluminescent horseradish peroxidase (HRP) substrate was purchased from Merck Millipore (United States). All other chemical reagents used were of analytical grade.

Production of Series of Mutants by in Silico Maturation

In the first cycle of sequence regulation by in silico maturation, a plurality of mutations were introduced into the sequence of a VEGF-binding aptamer (VEap121, SEQ ID NO:5) which was predicted to be folded to form a G-quadruplex structure. The sequence of VEap121 excluding the guanine bases responsible for maintenance of the quadruplex structure was randomly mutated to generate 10 kinds of VEap121 mutants. The VEGF-binding capacities of these 10 kinds of mutants were evaluated by a surface plasmon resonance (SPR) assay as described below. As a result, seven mutants were found to bind to VEGF, and these mutants were ranked based on their $K_d$ values.

For production of the second generation by in silico maturation, the top five mutants were selected from the first generation, and the sequences of these mutants were replicated at different appearance ratios depending on their ranks based on $K_d$. Random sequence pairs were extracted from these replicated sequences. Crossing-over was allowed to occur at a random point in each sequence pair, and two kinds of single-base mutations were randomly introduced to produce a group of 20 kinds of new sequences for the next generation.

In order to produce the third generation, the top five mutants were selected from the mutants evaluated in the first generation and the second generation. Crossing-over was allowed to occur at a random point between each of these five kinds of mutants and VEap121, and two kinds of single point mutations were randomly introduced to the resulting sequences. By repeating this process, 20 kinds of sequences were produced as the third generation.

Surface Plasmon Resonance Assay

The capacity of each oligonucleotide to bind to VEGF was evaluated using Biacore T200 (GE Healthcare Japan, Japan) by measuring SPR on a CM5 sensor chip. VEGF was dissolved in 10 mM acetate buffer (pH 6.0), and VEGF (about 1000 RU) was covalently bound to the CM5 sensor chip using an amine coupling kit. A non-labeled oligonucleotide (1 µM) was dissolved in Tris-buffered saline (TBS: 10 mM Tris-HCl, 100 mM NaCl, 5 mM KCl; pH 7.4), and the resulting solution was heated at 95° C. for 5 minutes, followed by allowing the solution to cool slowly. Under these conditions, each oligonucleotide is folded to form its specific secondary structure. Various concentrations of the oligonucleotide diluted with TBS was injected at a flow rate of 20 µl/minute at 20° C. onto the CM5 chip on which VEGF was immobilized. Binding between the immobilized VEGF and the oligonucleotide was monitored. By injecting NaCl (1 M), the CM5 chip was regenerated. Using Biacore evaluation software, the association rate and the dissociation rate were approximated to calculate the $K_d$ value.

Evaluation of VEGF-Binding Aptamers Based on Circular Dichroism

By measurement of the circular dichroism (CD) spectrum using a J-720 spectropolarimeter (JASCO, United States), the structure of each aptamer was analyzed. Total aptamer [final concentration (f.c.), 10 µM] was diluted with TBS, and folded by the heat treatment described above. In a 0.1-cm cell, the spectrum at 20° C. was recorded. Each spectrum was determined by averaging the results obtained by 20 times of scanning.

Construction of VEGF Detection System Using Improved Aptamer

Using an improved aptamer, a VEGF detection system was constructed. By adding FITC to the 5'-end, this aptamer was modified. Using TBS, a solution of a biotinylated anti-VEGF antibody (BAF293 (trade name), manufactured by R&D Systems, which is commercially available as a solution using 20 mM Tris buffer (pH 7.3) supplemented with 150 mM NaCl) at a final concentration of 40 ng/mL was prepared. Diluted BAF293 (100 µL) was added to a 96-well polystyrene plate (Nunc Immobilizer (registered trademark) #436015, Nunc) on which streptavidin is immobilized. This polystyrene plate was incubated for 30 minutes with gentle stirring, and the supernatant was then removed. After washing the plate, each well was filled with 100 µL of a 5-fold diluted blocking reagent N101 (Nitiyu, Japan) supplemented with 500 nM biotin, and incubated for 30 minutes. The addition of the blocking reagent (reagent containing a synthetic polymer) was carried out in order to reduce non-specific adsorption of protein to the polystyrene plate. The addition of biotin was carried out in order to inhibit excessive streptavidin on the polystyrene plate. Thereafter, the blocking reagent was removed from each well. The plate was then washed, and 100 µL of various concentrations of a protein (VEGF or BSA) was added to each well, followed by incubating the plate for 30 minutes. The wells were then washed three times. An FITC-labeled aptamer prepared with TBS (100 µL, 10 nM) after folding by heating was added to each well, and the plate was incubated for 30 minutes. After 3 times of washing, an HRP-conjugated anti-FITC antibody was added to each well, and the plate was incubated with gentle stirring for 30 minutes. Each well was then washed, and Immobilon Western chemiluminescent horseradish peroxidase (HRP) substrate was added thereto. The HRP activity was measured using a multilabel plate counter (Wallac 1420 ARVO MX, Perkin Elmer). During this assay, the wells were washed with TBST (TBS supplemented with 0.05% (v/v) Tween 20). All experimental operations were carried out at room temperature.

Results and Discussions

Improvement of Binding Capacity of VEGF Aptamer by in Silico Maturation

For use as a recognition element in a VEGF detection system, an aptamer having a high binding capacity to VEGF is required. $K_d$ of a VEGF aptamer (VEap121) confirmed in an earlier study[27] was reevaluated by an SPR assay (under the conditions described above). Since the calculated $K_d$ value of VEap121 was 4.7 nM, it was considered that the binding capacity of VEap121 needs to be improved for construction of a sensitive VEGF detection system. In view of this, the present inventors attempted to improve the binding capacity of VEap121 by in silico maturation. In silico maturation requires a plurality of sequences which function as parents (templates) and from which mutants are generated. For the first generation in the in silico maturation, mutated VEap121 sequences were used as parents. By randomly introducing mutations into the VEap121 sequences, a group of 10 kinds of oligonucleotide mutants were produced. Guanine bases were not changed. This is because guanine bases are considered to be necessary for folding of VEap121 into the G-quadruplex structure. After the synthesis, the binding capacities of the mutants to VEGF were evaluated by SPR. According to their $K_d$ values, the oligonucleotides were ranked. The VEGF-binding capacity of each oligonucleotide in each generation is shown in FIG. 1. Among the 10 kinds of VEap121 mutants in the first generation, 7 kinds showed the binding capacity to VEGF. The top five mutants were selected to be used as parents for the second generation.

In the production of the second generation, the top five sequences from the first generation were replicated into 40 kinds of sequences at different ratios depending on the VEGF-binding capacity. The ratios were as follows: the ratio of the first sequence, 12/40; the ratio of the second sequence, 10/40; the ratio of the third sequence, 8/40; and the ratio of each of the fourth and fifth sequences, 5/40. From this replication pool, two sequences were randomly selected, and the sequences were allowed to pair with each other. A random point was extracted from these sequences, and crossing-over was allowed to occur at this point between the sequences. Finally, a sequence was randomly extracted from this sequence pair, and two single-base random mutations was introduced thereto. By repeating this process, 20 kinds of sequences were obtained as the second generation. From evaluation using SPR, it was found that 5 kinds of mutants among them show the VEGF-binding capacity, while the others do not show the binding capacity. However, the binding capacities of the 5 mutants were lower than that of VEap121. These results indicate the possibility that VEap121 is relatively optimized for interaction with VEGF.

The 20 kinds of sequences were thus produced by crossing-over of VEap121, and the top five mutants in the first generation and the second generation that showed the binding capacity were selected for the third generation. Each mutant was replicated into 2 sequences, and crossing-over was allowed to occur between a replicated sequence and VEap121 at a random point. Subsequently, two single-base mutations were introduced into each sequence produced by the crossing-over. By repeating this process, 20 kinds of sequences were produced as the third generation. From the third generation, four kinds of oligonucleotides (3R02, 3R03, 3R08, and 3R09) that bind to VEGF more strongly than VEap121 were identified. Their base sequences are shown in SEQ ID NO:1 to SEQ ID NO:4, respectively. The base sequence of VEap121, which was used as the parent, is shown in SEQ ID NO:5. The sequence and the $K_d$ value of each of these oligonucleotides are shown below in Table 1. The $K_d$ value of each of 3R02, 3R03, 3R08, and 3R09 is shown below in Table 1 together with each base sequence (for example, "3R02" is represented as "3R#02" in Table 1). The Table 1 below also shows the base sequences and the $K_d$ values of a part of other oligonucleotides tested by the in silico maturation method. In Table 1, "n.d." means that the measurement was impossible, and indicates that there is no binding capacity to VEGF. In the base sequences, the Gs that are underlined and indicated in bold are Gs considered to be required for the G-quadruplex structure. The base sequences of 3R#01 to 3R#10 in Table 1 are shown in SEQ ID NO:7 to SEQ ID NO:14 in this order.

TABLE 1

| Name | Sequence (5' to 3') | $K_d$ |
|---|---|---|
| VEap121 | TGTGGGGGTGGACGGGCCGGGTAGA | 4.7 nM |
| 3R#02 | TGTGGGGGTGGACTGGGTGGGTACC | 300 pM |
| 3R#08 | TGTGGGGATGGATGGGCCGGGCTGC | 1.5 nM |
| 3R#03 | TGTGGGGGGTGGACGGGCCGAGTACG | 1.7 nM |

TABLE 1-continued

| Name  | Sequence (5' to 3')           | K_d    |
|-------|-------------------------------|--------|
| 3R#09 | TGTGGGGGTGGTTGGGCGGGGCTGC     | 2.4 nM |
| 3R#01 | TGTGGGGAGGACGGGCGGGGATGC      | 8.8 nM |
| 2R#08 | TGTGGGGTTGGACGGACCGGGTAGG     | n.d.   |
| 2R#10 | TGTGGGGTTGGACGGGCCGTGTAGA     | n.d.   |
| 2R#11 | TGTGGGGGTGCGCGGGCCGGGCAGG     | n.d.   |
| 3R#04 | TGTGCGGGGGGTGGGGGTGGTTCCC     | n.d.   |
| 3R#06 | TGTGGGGGGGGTGGGGGTGGACCGC     | n.d.   |
| 3R#07 | TGTGCGGGTGGCCGGGGTGGCCTGC     | n.d.   |
| 3R#10 | TGTGGGGCTGGGAGGTCGGGCCTGC     | n.d.   |

Figure 2:
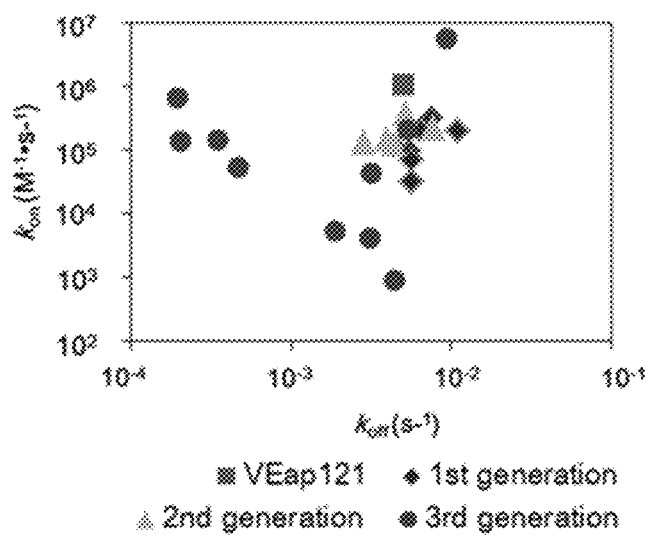
FIG. 2 is a diagram showing kinetic plots of VEGF-binding aptamers obtained in the Examples below. By measuring the SPR signal, all kinetic indices were calculated. The X-axis represents the dissociation rate constant, and the Y-axis represents the association rate constant.

As shown in Table 1, 3R02 (SEQ ID NO:1) showed the strongest binding capacity to VEGF. The $K_d$ value of 3R02 was 300 pM, and this indicates that 3R02 has 16 times higher binding capacity than VEap121. The dissociation rate constant ($k_{off}$) of 3R02 was $1.92 \times 10^4$ (M$^{-1}$ s$^{-1}$), and $k_{off}$ VEap121 was $4.99 \times 10^{-3}$ (M$^{-1}$) (FIG. 2). The association rate constant ($k_{on}$) of 3R02 was $6.39 \times 10^5$ (M$^{-1}$ s$^{-1}$), and $k_{on}$ of VEap121 was $1.05 \times 10^6$ (M$^{-1}$ s$^{-1}$). Thus, improvement of the VEGF-binding capacity could be achieved by decreasing the dissociation rate constant. The novel aptamer, which was missed in SELEX because of the limited number of candidates evaluated, could be obtained. This indicates that screening after SELEX based on in silico maturation is an effective method for improvement of the aptamer function.

Improvement of Binding Capacity of VEGF Aptamer by Dimerization

In previous studies, the present inventors reported improvement of a VEGF-binding aptamer by designing a bivalent aptamer (the references 27 and 38 listed below). In view of this, in the present study, the present inventors planned to further improve 3R02 by designing a bivalent aptamer. The designed bivalent aptamer (3R02 bivalent) has the base sequence of SEQ ID NO:6. Two monomer 3R02 oligonucleotides and a 10-mer thymine linker constitute 3R02 bivalent. From measurement of SPR, the $K_d$ value of 3R02 bivalent was calculated as 30 pM. By the dimerization of 3R02, the binding capacity could be improved 10-fold. Among the VEGF-binding DNA aptamers reported so far, 3R02 bivalent has the highest binding capacity, and its binding capacity is close to that of Macugen (registered trademark) (the reference 40 listed below), which is a VEGF-binding RNA aptamer known as an anti-VEGF therapeutic agent.

Measurement of CD Spectra of 3R02 and 3R02 Bivalent

Figure 3:
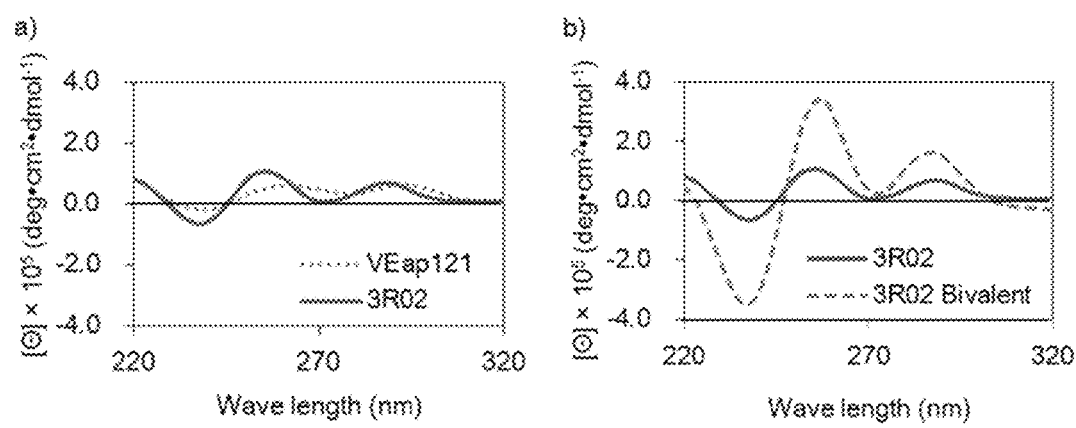
FIG. 3 is a diagram showing the CD spectra of the VEGF-binding aptamers obtained in the Examples below.

A CD spectrum is useful for collecting information related to the quadruplex structure of DNA. CD spectra were obtained for VEap121, 3R02, and 3R02 bivalent. VEap121 showed negative peaks at 239 nm and 280 nm, and positive peaks at 262 nm and 293 nm (FIG. 3a); and 3R02 showed negative peaks at 238 nm and 271 nm, and positive peaks at 256 nm and 288 nm (FIG. 3a). The intensity of the positive peak close to 260 nm in the CD spectrum of 3R02 was twice as high as the peak having the highest intensity in the spectrum of VEap121. Based on analysis using QGRS Mapper, VEap121 and 3R02 were predicted to have the same G-quadruplex motif (G1: 5'-nnnnggnnnggnnnnggnnng-gnnnn-3') (SEQ ID NO:15). However, data obtained from the CD spectra suggested that they have different G-quadruplex structures. The CD spectrum of 3R02 was the same as the spectrum of d(ggggtcaggctggggttgtgcaggtc) (SEQ ID NO: 16, the reference 41 listed below), which is folded to form an antiparallel G-quadruplex. Thus, it was hypothesized that 3R02 may form the same antiparallel G-quadruplex structure. The CD spectrum of 3R02 bivalent was also obtained. Since 3R02 contains two monovalent 3R02 sequences and a 10-mer thymine linker (T10), the T10 spectrum was subtracted from the 3R02 bivalent spectrum. The spectrum after the subtraction is shown in FIG. 3b. The spectrum after the subtraction showed a band pattern similar to that of 3R02, but the peak intensities of the spectrum was twice as high as the peak intensity of 3R02. This result indicates the possibility that 3R02 bivalent may contain two independent G-quadruplex structures of monovalent 3R02.

Construction of VEGF Detection System

Figure 4:
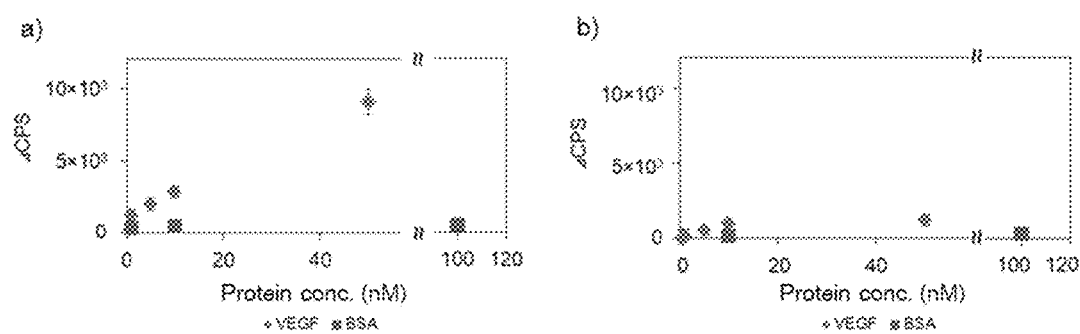
FIG. 4 is a diagram showing the results of measurement of VEGF by the plate assay using 3R02 (a) or VEap121 (b) carried out in the Examples below. An anti-VEGF antibody was immobilized on each well of a polystyrene plate using avidin biotin interaction. Various concentrations of VEGF dissolved in TBS was added to the wells. A solution of FITC-labeled 3R02 or VEap121 was added to each well. Chemiluminescence derived from an HRP-conjugated anti-FITC antibody, which indicates binding of FITC-labeled 3R02 to VEGF, was detected (n=3). As a control protein, BSA was used. The intensity of the chemiluminescence is represented as counts per second (CPS).

The present inventors attempted to improve the sensitivity of a VEGF detection system using the improved aptamer. Using an anti-VEGF antibody and 3R02 ($K_d$=300 pM), a VEGF detection system was constructed. The antibody was immobilized on a plate, and VEGF was then added thereto. Subsequently, FITC-labeled 3R02 was added to the plate. FITC-labeled 3R02 was then detected with an HRP-conjugated anti-FITC antibody. By this, a chemiluminescent signal from HRP, which indicates binding of 3R02 to VEGF and is dependent on the concentration of VEGF, is generated. LOD of this assay was 6.7 nM (FIG. 4a) as calculated from LOD=3 (SD/slope). "SD" was defined as the standard deviation in the reaction carried out with a VEGF concentration of 0 nM. "Slope" was defined as the slope of the calibration curve. Addition of BSA to the plate did not increase the signal. The plate assay was also carried out using VEap121 ($K_d$=4.7 nM) (FIG. 4b). Although a chemiluminescent signal from horseradish peroxidase, which indicates binding between the aptamer and VEGF, could be obtained, the intensity of the signal was one eighth of the signal obtained using 3R02. Saturation of the signal seemed to have occurred at a VEGF concentration of 10 nM, and the error bars of the data sets overlapped with each other. Thus, LOD of VEap121 could not be calculated. These results indicate that the use of 3R02 improved the sensitivity of the VEGF detection system.

A VEGF detection system was also constructed using 3R02 bivalent ($K_d$=30 pM), but the results were similar to those obtained with 3R02 (the data are shown in Fig. S-5 in Supporting Information). It was assumed that the antibody interferes with the binding between 3R02 bivalent and VEGF. In view of this, the present inventors consider that use of a VEGF antibody that binds to a different epitope may allow improvement of the sensitivity of the detection system.

REFERENCES (1) Savory, N.; Abe, K.; Sode, K.; Ikebukuro, K.: Selection of DNA aptamer against prostate specific antigen using a genetic algorithm and application to sensing. Biosens. Bioelectron. 2010. 26, 1386-1391.

(2) Ferrara, N.; Henzel, W. J.: Pituitary follicular cells secrete a novel heparin-binding growth factor specific for vascular endothelial cells. Biochem. Biophys. Res. Commun. 1989, 161, 851-858.

(3) Peirce, S. M.; Price, R. J.; Skalak, T. C.: Spatial and temporal control of angiogenesis and arterialization using focal applications of VEGF164 and Ang-1. Am. J. Physiol. Heart Circ. Physiol. 2004. 286, H918-925.

(4) Kim, K. J.; Li, B.; Winer, J.; Armanini, M.; Gillett, N.; Phillips, H. S.; Ferrara, N.: Inhibition of vascular endothelial growth factor-induced angiogenesis suppresses tumour growth in vivo. Nature 1993, 362, 841-844.

(5) Kondo, S.; Asano, M.; Matsuo, K.; Ohmori, I.; Suzuki, H.: Vascular endothelial growth factor/vascular permeability factor is detectable in the sera of tumor-bearing mice and cancer patients Biochim. Biophys. Acta 1994, 1221, 211-214.

(6) Stacker, S. A.; Baldwin, M. E.; Achen, M. G.: The role of tumor lymphangiogenesis in metastatic spread FASEB J. 2002, 16, 922-934.

(7) Rini, B. I.; Michaelson, M. D.; Rosenberg, J. E.; Bukowski, R. M.; Sosman, J. A.; Stadler, W. M.; Hutson, T. E.; Margolin, K.; Harmon, C. S.; DePrimo, S. E.; Kim, S. T.; Chen, I.; George, D. J.: Antitumor activity and biomarker analysis of sunitinib in patients with bevacizumab-refractory metastatic renal cell carcinoma. J. Clin. Oncol. 2008, 26, 3743-3748.

(8) Tolentino, M.: Systemic and ocular safety of intravitreal anti-VEGF therapies for ocular neovascular disease. Surv. Ophthalmol. 2011, 56, 95-113.

(9) Tuerk, C.; Gold, L.: Systematic evolution of ligands by exponential enrichment: RNA ligands to bacteriophage T4 DNA polymerase. Science 1990, 249, 505-510.

(10) Ellington, A. D.; Szostak, J. W.: In vitro selection of RNA molecules that bind specific ligands. Nature 1990, 346, 818-822.

(11) Ikebukuro, K.; Kiyohara, C.; Sode, K.: Electrochemical Detection of Protein Using a Double Aptamer Sandwich Anal. Lett. 2004, 37, 2901-2909.

(12) Ikebukuro, K.; Kiyohara, C.; Sode, K. Novel electrochemical sensor system for protein using the aptamers in sandwich manner. Biosens. Bioelectron. 2005, 20, 2168-2172.

(13) Potyrailo, R. A.; Conrad, R. C.; Ellington, A. D.; Hieftje, G. M. Adapting Selected Nucleic Acid Ligands (Aptamers) to Biosensors Anal. Chem. 1998, 70, 3419-3425.

(14) Lee, M.; Walt, D. R.: A fiber-optic microarray biosensor using aptamers as receptors. Anal. Biochem. 2000, 282, 142-146.

(15) Bruno, J. G.; Kiel, J. L.: Use of Magnetic Beads in Selection and Detection of Biotoxin Aptamers by Electrochemiluminescence and Enzymatic Methods. Biotechniques 2002, 32, 178-183

(16) Xiao, Y.; Lubin, A. A.; Heeger, A. J.; Plaxco, K. W.: Label-free electronic detection of thrombin in blood serum by using an aptamer-based sensor Angewandte Chemie 2005, 44, 5456-5459.

(17) Yoshida, W.; Sode, K.; Ikebukuro, K.: Aptameric enzyme subunit for biosensing based on enzymatic activity measurement. Anal. Chem. 2006, 78, 3296-3303.

(18) Ogasawara, D.; Hachiya, N. S.; Kaneko, K.; Sode, K.; Ikebukuro, K.: Detection system based on the conformational change in an aptamer and its application to simple bound/free separation. Biosens. Bioelectron. 2009, 24, 1372-1376.

(19) Carrasquillo, K. G.; Ricker, J. A.; Rigas, I. K.; Miller, J. W.; Gragoudas, E. S.; Adamis, A. P.: Controlled delivery of the anti-VEGF aptamer EYE001 with poly(lactic-co-glycolic)acid microspheres. Invest. Ophthalmol. Visual Sci. 2003, 44, 290-299.

(20) Burmeister, P. E.; Lewis, S. D.; Silva. R. F.; Preiss, J. R.; Horwitz, L. R.; Pendergrast, P. S.; McCauley, T. G.; Kurz, J. C.; Epstein, D. M.; Wilson, C.; Keefe, A. D.: Direct In Vitro Selection of a 2-O-Methyl Aptamer to VEGF Chem. Biol. 2005, 12, 25-33.

(21) Ng, E. W. M.; Shima, D. T.; Calias, P.; Cunningham, E. T.; Guyer, D. R.; Adamis, A. P.: Pegaptanib, a targeted anti-VEGF aptamer for ocular vascular disease. Nat. Rev. Drug Discovery 2006, 5, 123-132.

(22) Nick T. J.; Darugar, Q.; Kourentzi, K.; Willson, R. C.; Landes, C. F.: Dynamics of an anti-VEGF DNA aptamer: a single-molecule study. Biochem. Biophys. Res. Commun. 2008, 373, 213-218.

(23) Zhao, S.; Yang, W.; Lai, R. Y.: A folding-based electrochemical aptasensor for detection of vascular endothelial growth factor in human whole blood. Biosens. Bioelectron. 2011, 26, 2442-2447.

(24) Zhao, J.; He, X.; Bo, B.; Liu, X.; Yin, Y.; Li, G.: A "signal-on" electrochemical aptasensor for simultaneous detection of two tumor markers. Biosens. Bioelectron. 2012, 34, 249-252.

(25) Freeman, R.; Girsh, J.; Jou, A. F.; Ho, J. A.; Hug, T.; Dernedde, J.; Willner, I.: Optical aptasensors for the analysis of the vascular endothelial growth factor (VEGF). Anal. Chem. 2012, 84, 6192-6198.

(26) Hasegawa, H.; Sode, K.; Ikebukuro, K.: Selection of DNA aptamers against VEGF165 using a protein competitor and the aptamer blotting method. Biotechnol. Lett. 2008, 30, 829-834.

(27) Nonaka, Y.; Sode, K.; Ikebukuro, K.: Screening and improvement of an anti-VEGF DNA aptamer. Molecules 2010, 15, 215-225.

(28) Nonaka, Y.; Abe, K.; Ikebukuro, K.: Electrochemical Detection of Vascular Endothelial Growth Factor with Aptamer Sandwich Electrochemistry 2012, 80, 363-366.

(29) Klug, S. J.; Famulok, M.: All you wanted to know about SELEX. Mol. Biol. Rep. 1994, 20, 97-107.

(30) Polz, M.; Cavanaugh, C.: Bias in template-to-product ratios in multitemplate PCR Appl. Environ. Microb. 1998, 64, 3724-3730.

(31) Kanagawa, T.: Bias and artifacts in multitemplate polymerase chain reactions (PCR). J. Biosci. Bioeng. 2003, 96, 317-323.

(32) Ikebukuro, K.; Okumura, Y.; Sumikura, K.; Karube, I.: A novel method of screening thrombin-inhibiting DNA aptamers using an evolution-mimicking algorithm. Nucleic Acids Res. 2005, 33, e108.

(33) Noma, T.; Ikebukuro, K.: Aptamer selection based on inhibitory activity using an evolution-mimicking algorithm. Biochem. Biophys. Res. Commun. 2006, 347, 226-231.

(34) Noma, T.; Sode, K.; Ikebukuro, K.: Characterization and application of aptamers for Taq DNA polymerase selected using an evolution-mimicking algorithm. Biotechnol. Lett. 2006, 28, 1939-1944.

(35) Ikebukuro, K.; Yoshida, W.; Noma, T.; Sode, K.: Analysis of the evolution of the thrombin-inhibiting DNA aptamers using a genetic algorithm. Biotechnol. Lett. 2006, 28, 1933-1937.

(36) Kim, Y.; Cao, Z.; Tan, W.: Molecular assembly for high-performance bivalent nucleic acid inhibitor. PNAS 2008, 105, 5664-5669.

(37) Mallikaratchy, P. R.; Ruggiero, A.; Gardner, J. R.; Kuryavyi, V.; Maguire, W. F.; Heaney, M. L.; McDevitt, M. R.; Patel, D. J.; Scheinberg, D. A.: A multivalent DNA aptamer specific for the B-cell receptor on human lymphoma and leukemia. Nucleic Acids Res. 2011, 39, 2458-2469.

(38) Hasegawa, H.; Taira, K.; Sode, K.; Ikebukuro, K.: Improvement of Aptamer Affinity by Dimerization Sensors 2008, 8, 1090-1098.
(39) Kikin, O.; D'Antonio, L.; Bagga, P. S.: QGRS Mapper: a web-based server for predicting G-quadruplexes in nucleotide sequences. Nucleic Acids Res. 2006, 34, W676-682.
(40) Ruckman, J.; Green, L. S.; Beeson, J.; Waugh, S.; Gillette, W. L.; Henninger, D. D.; Claesson-Welsh, L.; Janjic, N.: 2'-Fluoropyrimidine RNA-based aptamers to the 165-amino acid form of vascular endothelial growth factor (VEGF165). Inhibition of receptor binding and VEGF-induced vascular permeability through interactions requiring the exon 7-encoded domain. J. biol. Chem. 1998, 273, 20556-20567.
(41) Wen, J. D.; Gray, D. M.: The Ff Gene 5 Single-Stranded DNA-Binding Protein Binds to the Transiently Folded Form of an Intramolecular G-Quadruplex Biochemistry 2002, 41, 11438-11448.

---

The invention claimed is:

1. A polynucleotide comprising the base sequence of any one of SEQ ID NOs:1 to 4, which polynucleotide binds to vascular endothelial growth factor.

2. The polynucleotide according to claim 1, comprising the base sequence of SEQ ID NO:1.

3. The polynucleotide according to claim 1, consisting of the base sequence of any one of SEQ ID NOs:1 to 4.

4. The polynucleotide according to claim 3, consisting of the base sequence of SEQ ID NO:1.

5. The polynucleotide according to claim 1, wherein a plurality of polynucleotide molecules each consisting of the base sequence of any one of SEQ ID NOs:1 to 4 are linked to each other directly or via a linker(s).

6. The polynucleotide according to claim 5, wherein two polynucleotides each consisting of the base sequence of SEQ ID NO:1 are linked to each other via a linker.

7. The polynucleotide according to claim 1, whose dissociation constant for vascular endothelial growth factor is less than 3 nM.

8. The polynucleotide according to claim 7, whose dissociation constant for vascular endothelial growth factor is less than 1 nM.

9. A method for measuring a concentration of vascular endothelial growth factor in a test sample, said method comprising bringing the polynucleotide according to claim 1 into contact with vascular endothelial growth factor, and measuring binding therebetween.

10. A kit for measuring a concentration of vascular endothelial growth factor, said kit comprising the polynucleotide according to claim 1.

11. The kit according to claim 10, comprising a labeled polynucleotide as said polynucleotide.

* * * * *

SEQUENCE LISTING

```
<160> NUMBER OF SEQ ID NOS: 16

<210> SEQ ID NO 1
<211> LENGTH: 25
<212> TYPE: DNA
<213> ORGANISM: artificial
<220> FEATURE:
<223> OTHER INFORMATION: VEGF-binding aptamer

<400> SEQUENCE: 1 tgtggggtg gactgggtgg gtacc                                           25

<210> SEQ ID NO 2
<211> LENGTH: 25
<212> TYPE: DNA
<213> ORGANISM: artificial
<220> FEATURE:
<223> OTHER INFORMATION: VEGF-binding aptamer

<400> SEQUENCE: 2 tgtggggtg gacgggccga gtacg                                           25

<210> SEQ ID NO 3
<211> LENGTH: 25
<212> TYPE: DNA
<213> ORGANISM: artificial
<220> FEATURE:
<223> OTHER INFORMATION: VEGF-binding aptamer

<400> SEQUENCE: 3
tgtggggatg gatgggccgg gctgc                                          25

<210> SEQ ID NO 4
<211> LENGTH: 25
<212> TYPE: DNA
<213> ORGANISM: artificial
<220> FEATURE:
<223> OTHER INFORMATION: VEGF-binding aptamer

<400> SEQUENCE: 4 tgtggggtg gttgggcggg gctgc                                           25

<210> SEQ ID NO 5
<211> LENGTH: 25
<212> TYPE: DNA
<213> ORGANISM: artificial
<220> FEATURE:
<223> OTHER INFORMATION: known VEGF-binding aptamer

<400> SEQUENCE: 5 tgtggggtg gacgggccgg gtaga                                           25

<210> SEQ ID NO 6
<211> LENGTH: 60
<212> TYPE: DNA
```

```
<213> ORGANISM: artificial
<220> FEATURE:
<223> OTHER INFORMATION: dimeric VEGF-binding aptamer

<400> SEQUENCE: 6 tgtggggtg gactgggtgg gtacctttt tttttgtgg gggtggactg ggtgggtacc    60

<210> SEQ ID NO 7
<211> LENGTH: 25
<212> TYPE: DNA
<213> ORGANISM: artificial
<220> FEATURE:
<223> OTHER INFORMATION: weakly VEGF-binding aptamer

<400> SEQUENCE: 7 tgtggggag gacgggcggg gatgc                                        25

<210> SEQ ID NO 8
<211> LENGTH: 25
<212> TYPE: DNA
<213> ORGANISM: artificial
<220> FEATURE:
<223> OTHER INFORMATION: non-VEGF-binding polynucleotide

<400> SEQUENCE: 8
tgtggggttg gacggaccgg gtagg                                       25

<210> SEQ ID NO 9
<211> LENGTH: 25
<212> TYPE: DNA
<213> ORGANISM: artificial
<220> FEATURE:
<223> OTHER INFORMATION: non-VEGF-binding polynucleotide

<400> SEQUENCE: 9
tgtggggttg gacgggccgt gtaga                                       25

<210> SEQ ID NO 10
<211> LENGTH: 25
<212> TYPE: DNA
<213> ORGANISM: artificial
<220> FEATURE:
<223> OTHER INFORMATION: non-VEGF-binding polynucleotide

<400> SEQUENCE: 10 tgtggggtg cgcgggccgg gcagg                                        25

<210> SEQ ID NO 11
<211> LENGTH: 25
<212> TYPE: DNA
<213> ORGANISM: artificial
<220> FEATURE:
<223> OTHER INFORMATION: non-VEGF-binding polynucleotide

<400> SEQUENCE: 11
tgtgcggggg gtggggtgg ttccc                                        25

<210> SEQ ID NO 12
<211> LENGTH: 25
<212> TYPE: DNA
<213> ORGANISM: artificial
<220> FEATURE:
<223> OTHER INFORMATION: non-VEGF-binding polynucleotide

<400> SEQUENCE: 12
tgtggggggg gtggggtgg accgc                                        25
```

```
<210> SEQ ID NO 13
<211> LENGTH: 25
<212> TYPE: DNA
<213> ORGANISM: artificial
<220> FEATURE:
<223> OTHER INFORMATION: non-VEGF-binding polynucleotide

<400> SEQUENCE: 13
tgtgcgggtg gccggggtgg cctgc                                    25

<210> SEQ ID NO 14
<211> LENGTH: 25
<212> TYPE: DNA
<213> ORGANISM: artificial
<220> FEATURE:
<223> OTHER INFORMATION: non-VEGF-binding polynucleotide

<400> SEQUENCE: 14
tgtggggctg ggaggtcggg cctgc                                    25

<210> SEQ ID NO 15
<211> LENGTH: 25
<212> TYPE: DNA
<213> ORGANISM: artificial
<220> FEATURE:
<223> OTHER INFORMATION: G-quadruplex motif
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (17)..(19)
<223> OTHER INFORMATION: n is a, c, g, or t
<220> FEATURE:
<221> NAME/KEY: misc_feature
<222> LOCATION: (22)..(25)
<223> OTHER INFORMATION: n is a, c, g, or t

<400> SEQUENCE: 15
nnnnggnnng gnnnggnnng gnnnn                                    25

<210> SEQ ID NO 16
<211> LENGTH: 26
<212> TYPE: DNA
<213> ORGANISM: artificial
<220> FEATURE:
<223> OTHER INFORMATION: polynucleotide with anti-parallel G-quadruplex
      structure

<400> SEQUENCE: 16
ggggtcaggc tggggttgtg caggtc                                   26
```